US010994262B2

(12) United States Patent
Kim et al.

(10) Patent No.: US 10,994,262 B2
(45) Date of Patent: May 4, 2021

(54) CATALYST FOR OXIDATIVE DEHYDROGENATION AND METHOD OF PREPARING THE SAME

(71) Applicant: LG CHEM, LTD., Seoul (KR)

(72) Inventors: Seongmin Kim, Daejeon (KR); Dong Hyun Ko, Daejeon (KR); Kyong Yong Cha, Daejeon (KR); Dae Heung Choi, Daejeon (KR); Myung Ji Suh, Daejeon (KR); Jun Kyu Han, Daejeon (KR); Sun Hwan Hwang, Daejeon (KR); Jun Han Kang, Daejeon (KR); Joo Hyuck Lee, Daejeon (KR); Hyun Seok Nam, Daejeon (KR); Ye Seul Hwang, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 425 days.

(21) Appl. No.: 15/765,445

(22) PCT Filed: May 18, 2017

(86) PCT No.: PCT/KR2017/005162

§ 371 (c)(1),
(2) Date: Apr. 2, 2018

(87) PCT Pub. No.: WO2017/213360

PCT Pub. Date: Dec. 14, 2017

(65) Prior Publication Data

US 2018/0290126 A1 Oct. 11, 2018

(30) Foreign Application Priority Data

Jun. 7, 2016 (KR) ........................ 10-2016-0070102

(51) Int. Cl.

| | |
|---|---|
| ***B01J 23/00*** | (2006.01) |
| ***B01J 23/72*** | (2006.01) |
| ***B01J 23/745*** | (2006.01) |
| ***B01J 23/75*** | (2006.01) |
| ***B01J 23/755*** | (2006.01) |
| ***B01J 23/78*** | (2006.01) |
| ***B01J 23/825*** | (2006.01) |
| ***B01J 23/83*** | (2006.01) |
| ***B01J 23/847*** | (2006.01) |
| ***B01J 23/86*** | (2006.01) |

(Continued)

(52) U.S. Cl.

CPC ............. *B01J 23/005* (2013.01); *B01J 21/04* (2013.01); *B01J 21/063* (2013.01); *B01J 21/066* (2013.01); *B01J 21/08* (2013.01); *B01J 21/16* (2013.01); *B01J 23/02* (2013.01); *B01J 23/06* (2013.01); *B01J 23/08* (2013.01); *B01J 23/10* (2013.01); *B01J 23/22* (2013.01); *B01J 23/26* (2013.01); *B01J 23/34* (2013.01); *B01J 23/72* (2013.01); *B01J 23/745* (2013.01); *B01J 23/75* (2013.01); *B01J 23/755* (2013.01); *B01J 23/78* (2013.01); *B01J 23/80* (2013.01); *B01J 23/825* (2013.01); *B01J 23/83* (2013.01); *B01J 23/8472* (2013.01); *B01J 23/86* (2013.01); *B01J 23/862* (2013.01); *B01J 23/864* (2013.01); *B01J 23/866* (2013.01); *B01J 23/868* (2013.01); *B01J 23/8892* (2013.01); *B01J 27/224* (2013.01); *B01J 27/24* (2013.01); *B01J 35/0013* (2013.01); *B01J 35/023* (2013.01); *B01J 37/0018* (2013.01); *B01J 37/0072* (2013.01); *B01J 37/0203* (2013.01); *B01J 37/0211* (2013.01); *B01J 37/0213* (2013.01); *B01J 37/0219* (2013.01); *B01J 37/0221* (2013.01); *B01J 37/08* (2013.01); *B01J 37/086* (2013.01); *B82Y 30/00* (2013.01); *B82Y 40/00* (2013.01); *C07C 5/48* (2013.01); *C07C 11/167* (2013.01); *B01J 35/002* (2013.01); *B01J 35/08* (2013.01); *B01J 2523/00* (2013.01); *B01J 2523/41* (2013.01)

(58) Field of Classification Search

CPC . B01J 23/80; B01J 23/005; B01J 21/04; B01J 21/08

See application file for complete search history.

(56) References Cited

U.S. PATENT DOCUMENTS 6,841,712 B1 * 1/2005 Iezzi ...................... B01J 8/0055 585/440
8,551,443 B2 10/2013 Mamedov et al.
(Continued)

FOREIGN PATENT DOCUMENTS

CN 1033013 5/1989
CN 1074631 7/1993
(Continued)

OTHER PUBLICATIONS

Blanco-Gutierrez et al. J. of Physical Chemistry, (2013), V.117, p. 20927-20935. (disclosed in IDS).*
(Continued)

*Primary Examiner* — Yong L Chu
(74) *Attorney, Agent, or Firm* — Dentons US LLP

(57) ABSTRACT

Disclosed are a catalyst for oxidative dehydrogenation and a method of preparing the same. More particularly, a catalyst for oxidative dehydrogenation of butene having a high butene conversion rate and superior side reaction inhibition effect and thus having high reactivity and high selectivity for a product by preparing metal oxide nanoparticles and then fixing the prepared metal oxide nanoparticles to a support, and a method of preparing the same are provided.

11 Claims, 2 Drawing Sheets

(51) Int. Cl.

| | |
|---|---|
| ***B01J 23/889*** | (2006.01) |
| ***B01J 21/04*** | (2006.01) |
| ***B01J 27/224*** | (2006.01) |
| ***B01J 37/02*** | (2006.01) |
| ***C07C 5/48*** | (2006.01) |
| ***C07C 11/167*** | (2006.01) |
| ***B01J 35/02*** | (2006.01) |
| ***B01J 23/02*** | (2006.01) |
| ***B01J 23/26*** | (2006.01) |
| ***B01J 37/00*** | (2006.01) |
| ***B01J 23/22*** | (2006.01) |
| ***B01J 37/08*** | (2006.01) |
| ***B01J 23/34*** | (2006.01) |
| ***B01J 23/10*** | (2006.01) |
| ***B01J 23/08*** | (2006.01) |
| ***B82Y 40/00*** | (2011.01) |
| ***B82Y 30/00*** | (2011.01) |
| ***B01J 35/00*** | (2006.01) |
| ***B01J 23/80*** | (2006.01) |
| ***B01J 23/06*** | (2006.01) |
| ***B01J 21/06*** | (2006.01) |
| ***B01J 21/08*** | (2006.01) |
| ***B01J 21/16*** | (2006.01) |
| ***B01J 27/24*** | (2006.01) |
| *B01J 35/08* | (2006.01) |

(56) References Cited

U.S. PATENT DOCUMENTS

| | | | |
|---|---|---|---|
| 8,674,156 | B2 | 3/2014 | Chung et al. |
| 2005/0211259 | A1 | 9/2005 | Gedevanishvili |

FOREIGN PATENT DOCUMENTS

| | | |
|---|---|---|
| CN | 100415653 | 9/2008 |
| CN | 101367702 | 2/2009 |
| CN | 103079695 | 5/2013 |
| CN | 103736489 | 4/2014 |
| CN | 104001533 | 8/2014 |
| CN | 104741123 | 7/2015 |
| EP | 2127788 | 12/2009 |
| KR | 10-0888143 | 3/2009 |
| KR | 10-1340620 | 12/2013 |
| WO | 2011027918 | 3/2011 |
| WO | 2014119870 | 8/2014 |

OTHER PUBLICATIONS

Lee et al. Catal. Lett., (2008), V.122, p. 281-286 (disclosed in IDS).*

Sun et al. JACS, (2004), V.126, p. 273-279 (disclosed in IDS).*

Koleva et al., Bulg. Chem. Commun., (2013), 45(4), p. 434-439.*

Kharisov et al., Arabian Journal of Chemistry, (2019), V.12, p. 1234-1246, published online on Nov. 26, 2014.*

Blanco-Guitierrez et al., "Magnetic Behavior of ZnFe2O4 Nanoparticles: Effects of a Solid Matrix and the Particle Size," J. Phys. Chem. C 114:1789-1795 (2010).

Sun et al., "Monodisperse MFe2O4 (M = Fe, Co, Mn) Nanoparticles," Journal of American Chemical Society 126: 273-279 (2004).

Lee et al., "Preparation of ZnFe2O4 Catalysts by a Co-precipitation Method Using Aqueous Buffer Solution and Their Catalytic Activity for Oxidative Dehydrogenation of n-Butene to 1,3-Butadiene," Catal. Lett. 122: 281-286 (2008).

Blanco-Guiterrez et al., "Superparamagnetic Behavior of MFe2O4 Nanoparticles and MFe2O4/SiO2 Composites (M: Co, Ni)," The Journal of Physical Chemistry C 117: 20927-20935 (2013).

Zhao et al., "Effect of surfactant amount on the morphology and magnetic properties of monodisperse ZnFe2O4 nanoparticles," Materials Research Bulletin 75: 172-177 (2016).

Rameshbabu et al., "Synthesis and Study of Structural, Morphological and Magnetic Properties of ZnFe2O4 Nanoparticles," J. Supercond. Nov. Magn. 27: 1499-1502 (2014).

Weijie et al., "Investigation of Support Effect of ZnFe2O4 and ZnCrFeO4 Catalysis," J. Molecular Catalysis 3(1): 10-21, published Mar. 31, 1989 [Original Document in Chinese, English Language Abstract included].

Mendonca, E. C., et al., "Size Effects on the Magnetic Properties of ZnFe2O4 Nanoparticles," J. Supercond Nov. Magn. (2013) 26:2329-2331.

* cited by examiner

【FIG. 1】
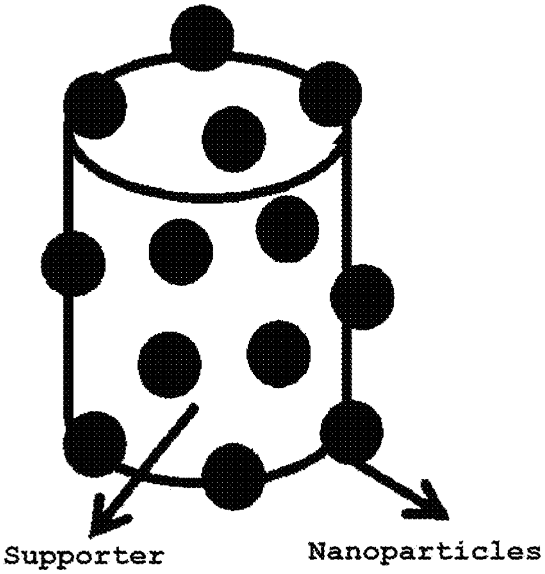
【FIG. 2】
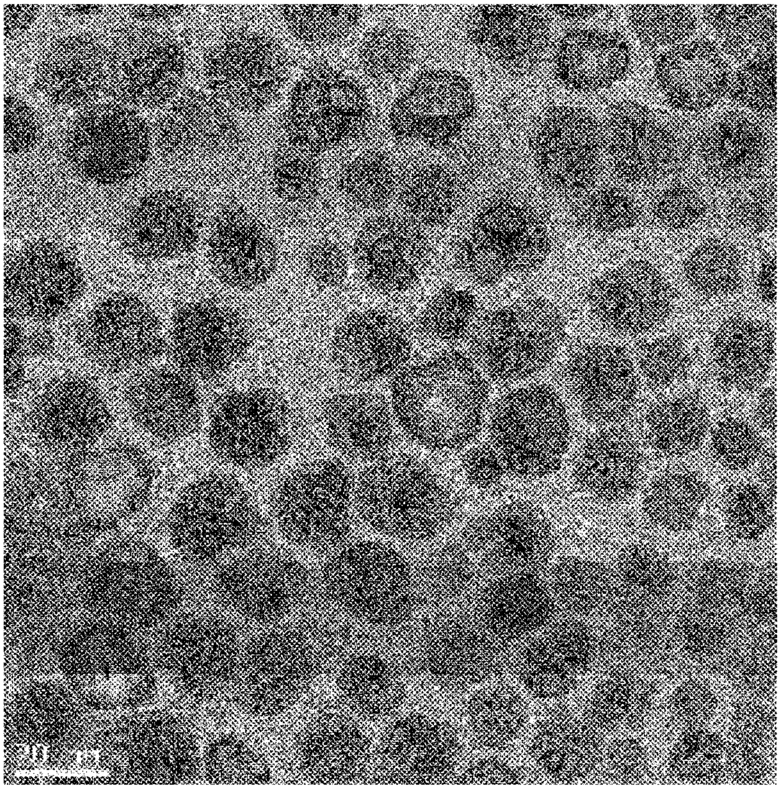

【FIG. 3】
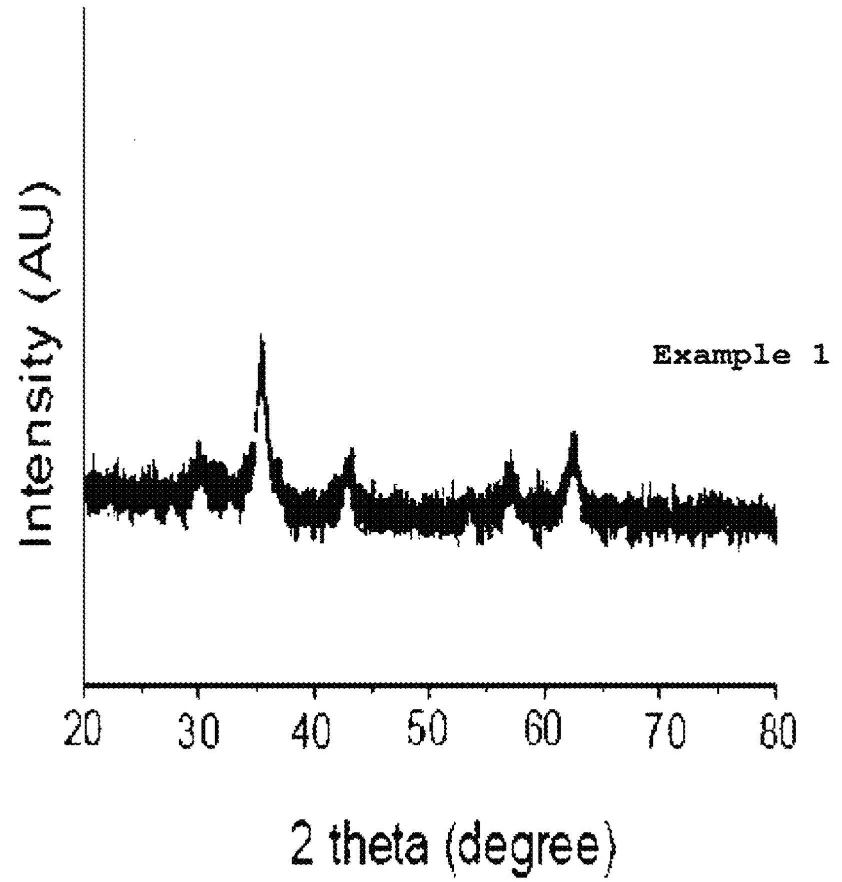
【FIG. 4】
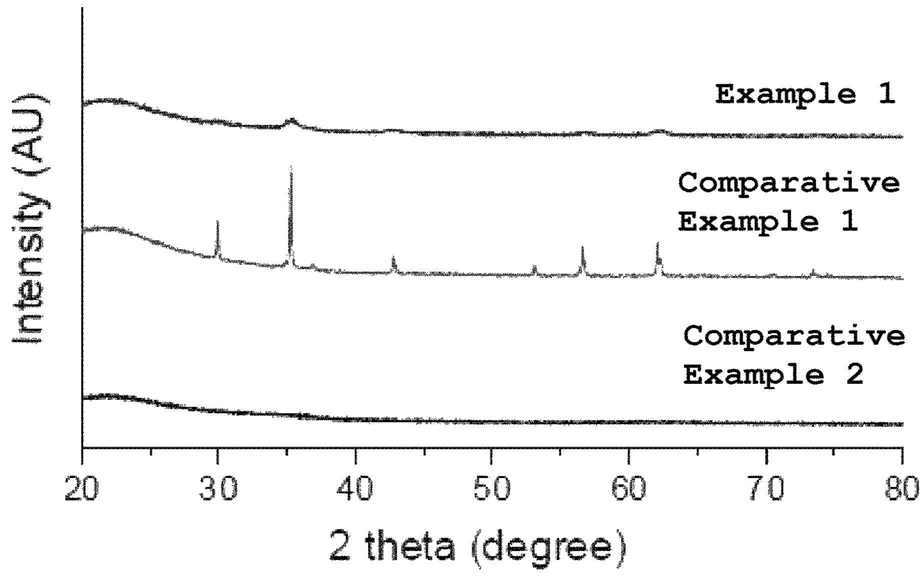

CATALYST FOR OXIDATIVE DEHYDROGENATION AND METHOD OF PREPARING THE SAME

CROSS-REFERENCE TO RELATED APPLICATION

This application is a National Stage Application of International Application No. PCT/KR2017/005162 filed on May 18, 2017, which claims priority to and the benefit of Korean Patent Application No. 10-2016-0070102, filed on Jun. 7, 2016, in the Korean Intellectual Property Office, both of which are incorporated herein in their entirety by reference for all purposes as if fully set forth herein.

TECHNICAL FIELD

The present invention relates to a catalyst for oxidative dehydrogenation and a method of preparing the same. More particularly, the present invention relates to a catalyst for oxidative dehydrogenation of butene having a high butene conversion rate and superior side reaction inhibition effect and thus having high reactivity and high selectivity for a product by preparing metal oxide nanoparticles and then fixing the prepared metal oxide nanoparticles to a support, and a method of preparing the same.

BACKGROUND ART

Demand for 1,3-butadiene, which is an intermediate in petrochemical products, and the value thereof are gradually increasing throughout the world. To produce such 1,3-butadiene, methods, such as naphtha cracking, direct butene dehydrogenation, and oxidative dehydrogenation of butene, have been used. However, in the case of naphtha cracking, energy consumption is high due to high reaction temperature. In addition, since naphtha cracking is not a process specifically designed for production of 1,3-butadiene production, other basic oils, other than 1,3-butadiene, are disadvantageously produced as surplus products. Meanwhile, direct dehydrogenation of normal-butene is thermodynamically unfavorable. In addition, since direct dehydrogenation of normal-butene is an endothermic reaction, high-temperature and low-pressure conditions are required to produce 1,3-butadiene in a high yield. Accordingly, direct dehydrogenation of normal-butene is not suitable as a commercial process for producing 1,3-butadiene.

Meanwhile, since, in the case of oxidative dehydrogenation of butene wherein butene reacts with oxygen in the presence of a metal oxide catalyst to generate 1,3-butadiene and water, stable water is generated, oxidative dehydrogenation of butene is thermodynamically advantageous. In addition, since oxidative dehydrogenation of butene is an exothermic reaction unlike direct dehydrogenation of butene, oxidative dehydrogenation of butene may produce 1,3-butadiene in a high yield even at low reaction temperature, compared to direct dehydrogenation of butene. In addition, since oxidative dehydrogenation of butene does not require additional heat supply, oxidative dehydrogenation of butene may be considered an effective production process that produces only 1,3-butadiene and thus satisfies demand for 1,3-butadiene.

Such a metal oxide catalyst is generally synthesized by a coprecipitation method of simultaneously precipitating a metal solution with a basic solution. However, upon bulk production of a metal oxide catalyst prepared by the coprecipitation method, uniformity thereof is poor due to different precipitation conditions of respective metal cations therein, and a surface area per unit volume thereof is small due to a size of several micrometers thereof. Such problems facilitate side reaction during oxidative dehydrogenation, and increase the amount of a catalyst used.

Therefore, there is an urgent need for development of a catalyst capable of being used in a reduced amount by inhibiting side reaction and having increased catalytic activity.

RELATED ART DOCUMENT

[Patent Document](Patent Document 1) KR0888143 B1

DISCLOSURE

Technical Problem

Therefore, the present invention has been made in view of the above problems, and it is one object of the present invention to provide a catalyst for oxidative dehydrogenation of butene having a high butene conversion rate and superior side reaction inhibition effect and thus having high reactivity and high selectivity for a product by preparing metal oxide nanoparticles with a spinel structure and then fixing the prepared metal oxide nanoparticles to a support.

The above and other objects can be accomplished by the present disclosure described below.

Technical Solution

In accordance with one aspect of the present invention, provided is a catalyst for oxidative dehydrogenation, including a metal oxide having a composition represented by Formula 1 below and an average particle diameter of 0.1 to 50 nm; and a support:

$AB_2O_4$ [Formula 1]

wherein A is, for example, one or more selected from the group consisting of divalent cationic metals and B is, for example, one or more selected from the group consisting of trivalent cationic metals.

In accordance with another aspect of the present invention, provided is a method of preparing a catalyst for oxidative dehydrogenation, wherein the method is performed by supporting or coating a nano-scale metal oxide on a support and includes a step of obtaining a mixed solution by mixing a precursor of divalent cationic metals (A), a precursor of trivalent cationic metals (B), an organic solvent, unsaturated fatty acid, and a surfactant and then heating the mixed solution at 100 to 350° C. to prepare a metal oxide having a composition represented by Formula 1 below and an average particle diameter of 0.1 to 50 nm:

Advantageous Effects

As apparent from the fore-going, the present invention advantageously provides a catalyst for oxidative dehydrogenation having superior side reaction inhibition effect, superior reactivity, and superior selectivity for a product due to inclusion of metal oxide nanoparticles, and a method of efficiently preparing the same.

DESCRIPTION OF DRAWINGS

FIG. 1 illustrates a schematic diagram of a preferred embodiment according to the present invention.

FIG. 2 illustrates a transmission electron microscope (TEM) photograph of metal oxide nanoparticles prepared according to the present invention.

FIG. 3 illustrates an X-ray diffraction result of metal oxide nanoparticles prepared according to the present invention.

FIG. 4 illustrates X-ray diffraction results of catalysts prepared according to the present invention and a conventional technology.

BEST MODE

Hereinafter, the present invention is described in detail.

The present inventors confirmed that, when a metal oxide is prepared using nanoparticles and the prepared metal oxide is coated or supported on a support to prepare a catalyst, a surface area per unit volume of the catalyst is increased during oxidative dehydrogenation, and thus, excellent reactivity and superior selectivity for a product are exhibited, thereby completing the present invention.

The oxidative dehydrogenation refers to a reaction of generating a conjugated diene and water through reaction between an olefin and oxygen in the presence of a metal oxide. In particular, the oxidative dehydrogenation may be a reaction of generating 1,3-butadiene and water through reaction between butene and oxygen.

A reactor used for the oxidative dehydrogenation is not specifically limited so long as it is suitable for oxidative dehydrogenation. For example, the reactor may be a reactor wherein a reaction temperature of an installed catalyst layer is maintained constant, and oxidative dehydrogenation is performed while reactants continuously pass through the catalyst layer. As a particular example, the reactor may be a tubular reactor, a batch reactor, a fluidized bed reactor, or a fixed bed reactor. Here, the fixed bed reactor may be, for example, a multi-tubular reactor or a plate-type reactor.

The reactants of the oxidative dehydrogenation may be, for example, one or more selected from the group consisting of butane, isobutane, 1-butene, trans-2-butene, and cis-2-butene and oxygen. In addition, the reactants may further include nitrogen and steam.

Now, the catalyst for oxidative dehydrogenation according to the present invention is described in detail.

The catalyst for oxidative dehydrogenation is characterized by including a metal oxide having a composition represented by Formula 1 below and an average particle diameter of 0.1 to 50 nm; and a support:

$AB_2O_4$ [Formula 1]

wherein A is, for example, one or more selected from the group consisting of divalent cationic metals, particularly one or more selected from the group consisting of Cu, Ra, Ba, Sr, Ca, Be, Fe(II), Zn, Mg, Mn, Co, and Ni, preferably one or more selected from the group consisting of Zn, Mg, Mn, Co, and Ni.

B is, for example, one or more selected from the group consisting of trivalent cationic metals, particularly one or more selected from the group consisting of Al, Fe(III), Cr, Si, V, Ga, In, La, and Ce, preferably one or more selected from the group consisting of Al, Fe(III) and Cr.

The metal oxide having the composition represented by Formula 1 may be, for example, a metal oxide having a spinel structure. The spinel structure may be understood as a structure wherein a unit lattice of a cubic system is composed of 8 divalent cations, 16 trivalent cations, and 32 oxygen ions, the oxygen ions mostly forming a face-centered cubic lattice and the divalent cations (A) and the trivalent cations (B) filling spaces between the oxygen ions.

The metal oxide may have, for example, an average particle diameter of 0.1 to 50 nm, or 1 to 30 nm. Within this range, a surface area per unit volume thereof is large, whereby excellent reactivity and excellent selectivity for a product may be provided during oxidative dehydrogenation.

A supporting amount or coating amount of the metal oxide may be, for example, 1 to 40 parts by weight, 5 to 30 parts by weight, or 5 to 20 parts by weight based on 100 parts by weight of the support included in the catalyst for oxidative dehydrogenation. Within this range, effective dispersion of nanoparticles may be provided.

The support is not specifically limited so long as a metal oxide may be supported or coated thereon. For example, the support may include one or more selected from the group consisting of alumina, silica, cordierite, titania, zirconia, silicon nitride, and silicon carbide.

FIG. 1 is a schematic diagram illustrating the shape of the catalyst for oxidative dehydrogenation according to the present invention. Referring to FIG. 1, the catalyst for oxidative dehydrogenation may have, for example, a form wherein the nano-scale metal oxide is uniformly distributed and supported or coated on the support.

The catalyst for oxidative dehydrogenation may be, for example, a supporting catalyst.

The catalyst for oxidative dehydrogenation according to the present invention has, for example, an average particle diameter of 0.1 to 50 nm, and thus, an increased surface area per unit volume compared to a bulk catalyst. Accordingly, in this range, the activity of the catalyst is increased and superior side reaction inhibition effect is exhibited, whereby superior reactivity and superior selectivity for a product are exhibited.

A method of preparing the catalyst for oxidative dehydrogenation according to the present invention is performed by supporting or coating a nano-scale metal oxide on a support and includes a step of obtaining a mixed solution by mixing a precursor of divalent cationic metals (A), a precursor of trivalent cationic metals (B), an organic solvent, unsaturated fatty acid, and a surfactant and then heating the mixed solution at 100 to 350° C. to prepare a metal oxide having a composition represented by Formula 1 below and an average particle diameter of 0.1 to 50 nm:

$AB_2O_4$ [Formula 1]

wherein A is, for example, one or more selected from the group consisting of divalent cationic metals, particularly one or more selected from the group consisting of Cu, Ra, Ba, Sr, Ca, Be, Fe(II), Zn, Mg, Mn, Co, and Ni, preferably one or more selected from the group consisting of Zn, Mg, Mn, Co, and Ni.

B is, for example, one or more selected from the group consisting of trivalent cationic metals, particularly one or more selected from the group consisting of Al, Fe(III), Cr, Si, V, Ga, In, La, and Ce, preferably one or more selected from the group consisting of Al, Fe(III) and Cr.

The divalent cationic metal (A) precursor may be selected, for example, from the group consisting of zinc acetate, zinc acetylacetonate, magnesium acetate, magnesium acetylacetonate, manganese acetate, manganese acetylacetonate, cobalt acetate, cobalt acetylacetonate, nickel acetate, and nickel acetylacetonate The trivalent cationic metal (B) precursor may be selected, for example, from the group consisting of aluminum acetate, aluminum acetylacetonate, iron acetate, iron acetylacetonate, chromium acetate, and chromium acetylacetonate.

For reference, in the present invention, it is not appropriate to use a chloride-based precursor as the metal precursor because it requires an additional process of generating a metal-oleate intermediate.

The divalent cationic metal (A) precursor and the precursor of trivalent cationic metals (B) may be dissolved, for example, in a molar ratio (B/A) of 1.5 to 10, 1.5 to 5, or 2 to 3 in an organic solvent. Within this range, single-phase metal oxide nanoparticles may be obtained.

The organic solvent may have, for example, a boiling point of 250° C. or more. In a particular example, as the organic solvent, hexadecane, hexadecene, octadecane, octadecene, phenanthrene, phenyl ether, octyl ether, benzyl ether, or the like may be used alone, or a mixture of two or more thereof may be used. For reference, when an organic solvent having a boiling point of less than 250° C. is used, generation and growth of metal oxide nanoparticles are insufficient, whereby particles are not sufficiently generated.

The unsaturated fatty acid and the surfactant control entanglement of metal oxide nanoparticles during high-temperature decomposition in an organic solvent. Accordingly, an average particle diameter of metal oxide nanoparticles may be adjusted by controlling a ratio of the unsaturated fatty acid to the surfactant which are added to an organic solvent. Preferably, the unsaturated fatty acid and the surfactant are previously mixed in an organic solvent to be used considering dispersion of a precursor. Here, the unsaturated fatty acid and the surfactant may be included in a total content of 1 to 60 parts by weight, or 3 to 60 parts by weight based on 100 parts by weight of the organic solvent.

As a particular example, the unsaturated fatty acid may be included in an amount of 3 to 30 parts by weight and the surfactant may be included in an amount of 3 to 30 parts by weight based on 100 parts by weight of the organic solvent.

For example, as the unsaturated fatty acid, lauric acid, palmitic acid, oleic acid, stearic acid, or the like may be used alone, or a mixture of two or more thereof may be used.

For example, as the surfactant, octylamine, trioctylamine, decylamine, dodecylamine, tetradecylamine, hexadecylamine, oleylamine, octadecylamine, tribenzylamine, triphenylamine, or the like may be used alone, or a mixture of two or more thereof may be used.

With regard to use of the unsaturated fatty acid and the surfactant, oleic acid and oleylamine may be used in various combinations based on the following application examples. For example, the oleic acid to oleylamine may be included in a molar ratio of 1:1 to 10:1, 1:1 to 5:1, or 1:1 to 2:1. Within this range, an average particle diameter may be efficiently adjusted while preventing entanglement of the metal oxide nanoparticles. For reference, when the molar ratio exceeds the upper limit value, a sample is used in a greater amount than necessary amount, whereby particle diameter adjustment is decreased and is not economical. When the molar ratio is less than the lower limit value, particles are agglomerated, whereby particles might not be provided in a uniform size.

Subsequently, the mixed solution is heated to 100 to 350° C. to prepare a metal oxide having a composition represented by Formula 1 below and an average particle diameter of 0.1 to 50 nm. The heating is preferably performed in a multistage manner so as to prepare particles having a uniform size and composition. For example, the heating may be performed by elevating temperature up to 100° C. or more, or 100 to 120° C. at a temperature elevation rate of 1 to 10° C./min and maintaining the elevated temperature for 30 minutes to 1 hour, followed by elevating temperature up to 190° C. or more, or 190 to 210° C. at a temperature elevation rate of 1 to 10° C./min and maintaining the elevated temperature for 1 hour to 2 hours.

Subsequently, the solution is heated up to 290° C. or more, or 290 to 310° C. at a temperature elevation rate of 1 to 5° C./min, and then refluxed for 1 hour to 2 hours.

The step of supporting and coating the metal oxide nanoparticles on the support to provide the catalyst for oxidative dehydrogenation of the present invention aims to uniformly spray particles on a structure, and may be suitably modified based on conditions used in the art.

For example, after the step of supporting or coating the metal oxide nanoparticles on the support, a step of drying the supported or coated support may be included. After the drying step, a firing step may be further included as needed.

In another embodiment, the metal oxide nanoparticles may be dispersed in a solvent having a boiling point of 69° C. or less, such as hexane or methylpentane, and then supported on a support, followed by being slowly dried at a temperature less than the boiling point of the used solvent. Accordingly, the metal oxide nanoparticles may be satisfactorily fixed to the support while being uniformly dispersed on the support, whereby catalyst reaction may be effectively performed without desorption of the metal oxide nanoparticles during subsequent oxidative dehydrogenation.

For example, the drying may be performed at room temperature to 62° C., or 40 to 60° C.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Example 1

20 ml of octyl ether as an organic solvent, 4 mmol of oleic acid as unsaturated fatty acid, and 4 mmol of oleylamine as a surfactant were fed into a flask, and then mixed.

2.507 g of a powder-type zinc acetylacetonate ($Zn(C_5H_7O_2)_2$), as the divalent cationic metal (A) precursor, and 3.053 g of a powder-type iron acetylacetonate ($Fe(C_5H_7O_2)_3$), as the trivalent cationic metal (B) precursor, were added to the mixed solution (in a molar ratio of Zn:Fe=1:2), and reacted at 110° C. for one hour, whereby thereby surplus water and oxygen were removed.

Subsequently, temperature was elevated up to 200° C. and the elevated temperature was maintained for two hours. Subsequently, temperature was elevated up to 300° C., and the elevated temperature was maintained for one hour, followed by cooling. Subsequently, a recovery process was performed.

A transmission electron microscope (TEM) photograph of the prepared metal oxide nanoparticles is illustrated in FIG. 2. Referring to FIG. 2, nanoparticles having a uniform average particle diameter of 14 nm were prepared. An XRD analysis result of the prepared metal oxide nanoparticles is illustrated in FIG. 3. Referring to FIG. 3, it was confirmed that the metal oxide nanoparticles had a spinel structure of $ZnFe_2O_4$.

The metal oxide nanoparticles were dispersed in hexane, and then supported on a silica support (silica gel 60, Merck) by impregnation, followed by being dried at 60° C. Here, 10 parts by weight of the metal oxide nanoparticles were supported on 100 parts by weight of the support.

An X-ray diffraction analysis pattern of the prepared catalyst is illustrated in FIG. 4. It was confirmed that, after the supporting, the nanoparticles having a spinel structure were distributed on the support. In addition, it was confirmed by the X-ray diffraction analysis that the nanoparticles had a particle size of 17 nm (see Table 1).

Example 2

A catalyst was prepared in the same manner as in Example 1, except that oleic acid and oleylamine were respectively used in an amount of 6 mmol.

Example 3

A catalyst was prepared in the same manner as in Example 1, except that oleic acid and oleylamine were respectively used in an amount of 8 mmol.

Comparative Example 1

$ZnFe_2O_4$, as a commercially available spinel oxide, and a silica support (silica gel, 60, Merck) were respectively fired at 600° C. Subsequently, 10 parts by weight of $ZnFe_2O_4$ were mixed with 100 parts by weight of the silica support, and the resultant mixture was used in an experiment. An X-ray diffraction analysis pattern of the prepared catalyst is illustrated in FIG. 4. It was confirmed by the X-ray diffraction analysis that resultant nanoparticles had an average particle diameter of 90 nm (see Table 1).

Comparative Example 2

200 g of distilled water was fed into a flask, and 0.28 g of zinc chloride ($ZnCl_2$) and 1.13 g of ferric chloride ($FeCl_3$) were fed thereinto, followed by mixing to prepare a mixture. The mixture was impregnated with the same support as that used in Example 1.

The impregnated solution was dried at 90° C., and then fired at 600° C., thereby preparing a catalyst. Here, 10 parts by weight of the metal oxide were supported on 100 parts by weight of the support. An X-ray diffraction analysis pattern of the prepared catalyst is illustrated in FIG. 4. In the case of Comparative Example 2, the particles were uniformly distributed on a surface of the structure, and thus, a diffraction size could not be measured.

The metal oxides prepared according to each of Examples 1 to 3 and Comparative Example 1 are summarized in Table 1 below.

TABLE 1

| Classification | Particle size (nm) |
|---|---|
| Example 1 | 17 |
| Example 2 | 14 |
| Example 3 | 10 |
| Comparative Example 1 | 90 |

Test Example

Using the catalyst for oxidative dehydrogenation prepared according to each of Example 1 and Comparative Examples 1 and 2, butadiene was prepared by the following method. Results are summarized in Table 2 below.

Butadiene Preparation

A mixture of trans-2-butene and cis-2-butene and oxygen were used as reactants, and, additionally, nitrogen and steam were introduced together thereinto. As a reaction composition, a volumetric ratio of oxygen to nitrogen to steam was 1 to 4 to 5. Butene was composed of trans-2-butene and cis-2-butene which were mixed in a volumetric ratio of 60% to 40%. Reaction was performed under conditions of a gas hourly space velocity (GHSV) of 125 and a reaction temperature of 400° C. on a butene basis. As a reactor, a metallic tubular fixed bed reactor was used. The metallic tubular fixed bed reactor was charged with 2 cc of the catalyst prepared according to each of the example and the comparative examples, and water steam was injected thereinto. With regard to the water steam injection, water was vaporized into steam at 120° C. by means of a vaporizer, and the steam was mixed with a butene mixture and oxygen, as reactants, followed by being introduced together into the reactor. After reaction, a product was analyzed by gas chromatography (GC). A butene conversion rate, a butadiene selectivity, a COx selectivity, and a yield were respectively calculated according to the following Mathematical Equations 1 to 4 based on results measured by gas chromatography:

Conversion rate (%)=(moles of fed butene/moles of reacted butene)×100 [Mathematical Equation 1]

Butadiene selectivity (%)=(moles of generated 1,3-butadiene/moles of reacted butene)×100 [Mathematical Equation 2]

COx selectivity (%)=[(moles of generated $CO_2$+moles of CO)/4)/moles of reacted butene]×100 [Mathematical Equation 3]

Yield (%)=(moles of generated 1,3-butadiene/moles of fed butene)×100 [Mathematical Equation 4]

TABLE 2

| Classification | Butene conversion rate (%) | Butadiene selectivity (%) | COx selectivity (%) | Butadiene yield (%) |
|---|---|---|---|---|
| Example 1 | 64.1 | 83.6 | 11.2 | 53.6 |
| Comparative Example 1 | 6.4 | 57.5 | 17.0 | 3.7 |
| Comparative Example 2 | 32.1 | 41.9 | 30.2 | 13.4 |

As shown in Table 2, it can be confirmed that, in the case of Example 1 prepared according to the present invention, a high butene conversion rate and high butadiene selectivity are exhibited. It can be confirmed that, in the case of Comparative Example 2 prepared according to a conventional method, COx, as a byproduct, is generated in a large amount in the supporting catalyst. In addition, it can be confirmed that the catalyst according to Comparative Example 1 in which a commercially available $ZnFe_2O_4$ was used as a metal oxide has a large particle size, whereby both a butene conversion rate and a butadiene yield are reduced.

In conclusion, it can be confirmed that, when a metal oxide is used as nanoparticles, and oxidative dehydrogenation is performed using a catalyst prepared by coating or supporting the metal oxide on a support so as to prepare a catalyst for oxidative dehydrogenation, a catalyst having an excellent reactant conversion rate, being capable of inhibiting generation of COx, as a byproduct, and having superior selectivity for butadiene, as a product, may be realized due to a large surface area per unit volume of the catalyst.

The invention claimed is:

1. A catalyst for oxidative dehydrogenation, comprising:

a support consisting of one or more selected from the group consisting of silica, cordierite, titania, zirconia, silicon nitride, and silicon carbide; and a plurality of metal oxide particles having a composition of Formula 1 below and an average particle diameter of 0.1 to 50 nm uniformly coated or distributed on a surface of the support:

$AB_2O_4$ [Formula 1]

wherein A is one or more selected from the group consisting of Cu, Ra, Ba, Sr, Ca, Be, Zn, and Mg, and B is one or more selected from the group consisting of trivalent cationic metals, and wherein the metal oxide particles are included in an amount of 5 to 20 parts by weight based on 100 parts by weight of the support, and wherein the catalyst exhibits selectivity for butadiene in an oxidative dehydrogenation conversion of butene and inhibits generation of CO and/or $CO_2$ as a byproduct.

2. The catalyst according to claim 1, wherein B is one or more selected from the group consisting of Al, Fe(III), Cr, V, Ga, In, La, and Ce.

3. The catalyst according to claim 1, wherein the catalyst is a supporting catalyst or a coating catalyst.

4. A method of preparing a catalyst for oxidative dehydrogenation, wherein the method is performed by supporting or coating a nano-scale metal oxide on a support consisting of one or more selected from the group consisting of silica, cordierite, titania, zirconia, silicon nitride, and silicon carbide, the method comprising:

obtaining a mixed solution by mixing a precursor of divalent cationic metals (A), a precursor of trivalent cationic metals (B), an unsaturated fatty acid, a surfactant, and an organic solvent that is one or more selected from the group consisting of hexadecane, hexadecene, octadecane, octadecene, and octyl ether; and heating the mixed solution by elevating a temperature up to 100° C. to 120° C. at a temperature elevation rate of 1 to 10° C./min and maintaining the elevated temperature for 30 minutes to 1 hour to remove water and oxygen, followed by elevating the temperature up to 190° C. to 210° C. at a temperature elevation rate of 1 to 10° C./min and maintaining the elevated temperature for 1 hour to 2 hours, and subsequently heating up to 290° C. to 310° C. at a temperature elevation rate of 1 to 5° C./min, and then refluxing for 1 hour to 2 hours to prepare the nano-scale metal oxide having a composition of Formula 1 below and an average particle diameter of 0.1 to 50 nm:

$AB_2O_4$ [Formula 1]

wherein A is one or more selected from the group consisting of Cu, Ra, Ba, Sr, Ca, Be, Zn, and Mg, and B is one or more selected from the group consisting of trivalent cationic metals;

dispersing the nano-scale metal oxide in a solvent having a boiling point of 69° C. or less to form a dispersion of the nano-scale metal oxide;

coating the dispersion of the nano-scale metal oxide on the support; and drying the support coated with the dispersion of the nano-scale metal oxide at a temperature of 40° C. to 60° C.

5. The method according to claim 4, wherein the divalent cationic metal (A) precursor is selected from the group consisting of zinc acetate, zinc acetylacetonate, magnesium acetate, and magnesium acetylacetonate.

6. The method according to claim 4, wherein the trivalent cationic metal (B) precursor is selected from the group consisting of aluminum acetate, aluminum acetylacetonate, iron acetate, iron acetylacetonate, chromium acetate, and chromium acetylacetonate.

7. The method according to claim 4, wherein the divalent cationic metal (A) precursor and the trivalent cationic metal (B) precursor are mixed in a molar ratio (B/A) of 1.5 to 3.

8. The method according to claim 4, wherein the unsaturated fatty acid is one or more selected from the group consisting of lauric acid, palmitic acid, oleic acid, and stearic acid.

9. The method according to claim 4, wherein the surfactant is one or more selected from the group consisting of octylamine, trioctylamine, decylamine, dodecylamine, tetradecylamine, hexadecylamine, oleylamine, octadecylamine, tribenzylamine, and triphenylamine.

10. The method according to claim 4, wherein a molar ratio of the unsaturated fatty acid to the surfactant is 1:1 to 10:1.

11. The method according to claim 4, wherein the solvent having a boiling point of 69° C. or less is hexane or methylpentane.

* * * * *